United States Patent [19]
Reid

[11] Patent Number: 5,081,863
[45] Date of Patent: * Jan. 21, 1992

[54] APPARATUS FOR MEASURING TRANSMISSION OF VOLATILE SUBSTANCES THROUGH FILMS

[75] Inventor: Philip L. Reid, Duncan, S.C.

[73] Assignee: Modern Controls, Inc., Minneapolis, Minn.

[*] Notice: The portion of the term of this patent subsequent to Aug. 14, 2001 has been disclaimed.

[21] Appl. No.: 649,191

[22] Filed: Feb. 4, 1991

Related U.S. Application Data

[63] Continuation of Ser. No. 383,226, Jul. 19, 1989, abandoned, which is a continuation of Ser. No. 5,224, Mar. 2, 1987, abandoned, which is a continuation of Ser. No. 740,187, May 31, 1985, Pat. No. 4,660,441.

[51] Int. Cl.$^5$ ............................................. G01N 15/08
[52] U.S. Cl. ......................................................... 73/38
[58] Field of Search ............................................. 73/38

[56] References Cited

U.S. PATENT DOCUMENTS

| | | | |
|---|---|---|---|
| 1,827,562 | 10/1931 | Carpenter | 73/38 |
| 3,498,110 | 3/1970 | Brun | 73/38 |
| 3,590,634 | 7/1971 | Pasternak | 73/38 |
| 3,604,246 | 9/1971 | Toren | 73/38 |
| 3,618,361 | 11/1971 | Stephens et al. | 73/38 |
| 3,668,928 | 6/1972 | Strydom | 73/38 |
| 4,385,517 | 5/1983 | Sorce et al. | 73/38 |
| 4,391,128 | 7/1983 | McWhorter | 73/38 |
| 4,464,927 | 8/1984 | Reid | 73/38 |
| 4,468,951 | 9/1984 | Garcia et al. | 73/38 |
| 4,660,411 | 4/1987 | Reid | 73/38 |

FOREIGN PATENT DOCUMENTS 435171  2/1925  Fed. Rep. of Germany .......... 73/38

OTHER PUBLICATIONS

Mocon Modern Control, Inc.; The New Ox-Tran 100 Twin; Sales Brochure.
Mocon Modern Control, Inc.; Ox-Tran 10/50, Sales Brochure.

Primary Examiner—John E Chapman
Attorney, Agent, or Firm—Bailey & Hardaway

[57] ABSTRACT

An apparatus for measuring gas transmission through films and membranes comprises upper and lower staging sections with sample sites defined therebetween. The upper and lower staging sections communicate with sample sites of transmitted gas and carrier gases and a volatile substance can be positioned in sample sites of the upper staging section.

1 Claim, 5 Drawing Sheets

APPARATUS FOR MEASURING TRANSMISSION OF VOLATILE SUBSTANCES THROUGH FILMS

This application is a continuation of application Ser. No. 07/383,226, filed Jul. 19, 1989, abandoned which is a continuation of application Ser. No. 005,224, filed Mar. 2, 1987, now abandoned which is a con of 06/740,187, filed May 31, 1985 which is now U.S. Pat. No. 4,660,411.

BACKGROUND OF THE INVENTION

This invention relates generally to the art of measuring gas transmission through solid material and more particularly to an apparatus for quantitatively measuring gas transmission through films and membranes.

In many areas of technology, it is highly desirable to know in advance the gas transmission rate through the various films and membranes. In the packaging industry in particular and in the art of food packaging, as well as in the containment of most biological and phaseological materials, it is highly important to utilize materials which will not permit the permeation of atmospheric gases which will deleteriously affect the packaged substance. Various substances are affected differently by differing gases.

Food products and meats in particular are better preserved in the absence of oxygen. It is thus important that packaging materials be utilized which have a very low rate of transmission for atmospheric oxygen. Other products may be deleteriously affected by the presence of carbon monoxide or carbon dioxide. In any event in order to appropriately select packaging materials, it is necessary that gas transmission rates of interest be known and thus capable of measurement.

Prior to the invention disclosed herein, such measurements have been performed on packaging films within laboratories on a largely manual basis, wherein closed volumes were separated from one another by a film sample. One closed containment volume would either be continuously flushed with and/or closed with the gas whose transmission rate was being measured while the other chamber would contain an inert or carrier gas. At specified periods of time the carrier gas side would be connected to varying types of measuring means to detect the quantity of transmitted gas therein. This measurement process would be repeated on the same sample and on varying samples for varying periods of time until some reproduceability was achieved. This process, however, is manually performed and thus is highly dependent upon the skill of the operator in that precise timing is required for the manipulation of valves and measuring equipment. Additional variables related to the manual operation are the placement of the sample between the two volumes and the detection equipment utilized for detecting the presence of the transmitted gas.

Frequently laboratory arrangements such as that described above are capable of detecting only the presence of a single transmitted gas and would thus not be useful for detecting the presence of any other gas.

My issued U.S. Pat. No. 4,464,927 describes an apparatus for measuring gas transmissions through film materials. However, this apparatus, as well as other prior art apparatus, have not been able to measure the transmission rates of volatile solids and liquids through such films.

SUMMARY OF THE INVENTION

It is thus an object of this invention to provide a novel apparatus for measuring the transmission of gases and volatile substances through films and membranes.

It is a further object of this invention to provide such an apparatus for performing such measurements which operates on an automated basis.

It is a still further and more particular object of this invention to provide such apparatus which is capable of performing such measurements on a plurality of samples simultaneously.

It is a yet further object of this invention to provide such an apparatus which is capable of producing measurements with a variety of volatile substances.

These as well as other objects are accomplished by an apparatus having a lower staging section with a plurality of sample sites having conduit means in communication with each sample site for providing a flow of gas into and out of the sample site with means for interrupting flow through the conduit means and with a removable upper staging section having complementary samples sites therein and conduit means connecting the sample sites for permitting a flow of gas through the sample sites. The sample site of the upper staging section includes means for placement of a volatile solid or liquid within the sample site. Means are provided for aligning the upper and lower staging sections so as to trap samples at each sample site. The conduit means of the lower staging section communicate with detection means for measuring the quantity of transmitted gas or volatile substance passing through the sample from the upper staging section into the lower staging section. The means for interrupting the flow of gas into and out of the sample sites of the lower staging section communicate with automated means for opening and closing the means for interrupting on a periodic basis.

DETAILED DESCRIPTION

In accordance with this invention, it has been found that gas transmission rates may be readily and reproduceably measured utilizing an apparatus in accordance with this invention. As used within this description the term "gas transmission rate" means the rate of gas transmission generally, as well as the transmission rate of volatile substances through the appropriate film or membrane. Examples of volatile liquid and solid substances whose transmission rate is measured by the apparatus of this invention include such odoriferous materials as chocolate, various perfumes, and food flavorings. The apparatus of this invention thus possesses utility for the measurement of transmission rates of deleterious substances into packaging, as well as the ability of the packaging to maintain volatiles given off from liquids and solids of the type above described.

The apparatus in accordance with this invention is automated so as to eliminate to a major extent the manual task required for such measurements and the shortcomings associated therewith. It has been surprisingly found that the apparatus in accordance with this invention possesses the ability to reproducibly detect and measure transmission rates with an accuracy not heretofore available. This unexpected aspect of this invention is most apparent when measuring extremely low transmission rates. Various other advantages will become apparent from the following detailed description with reference to the various Figures of drawing.

Figure 1:
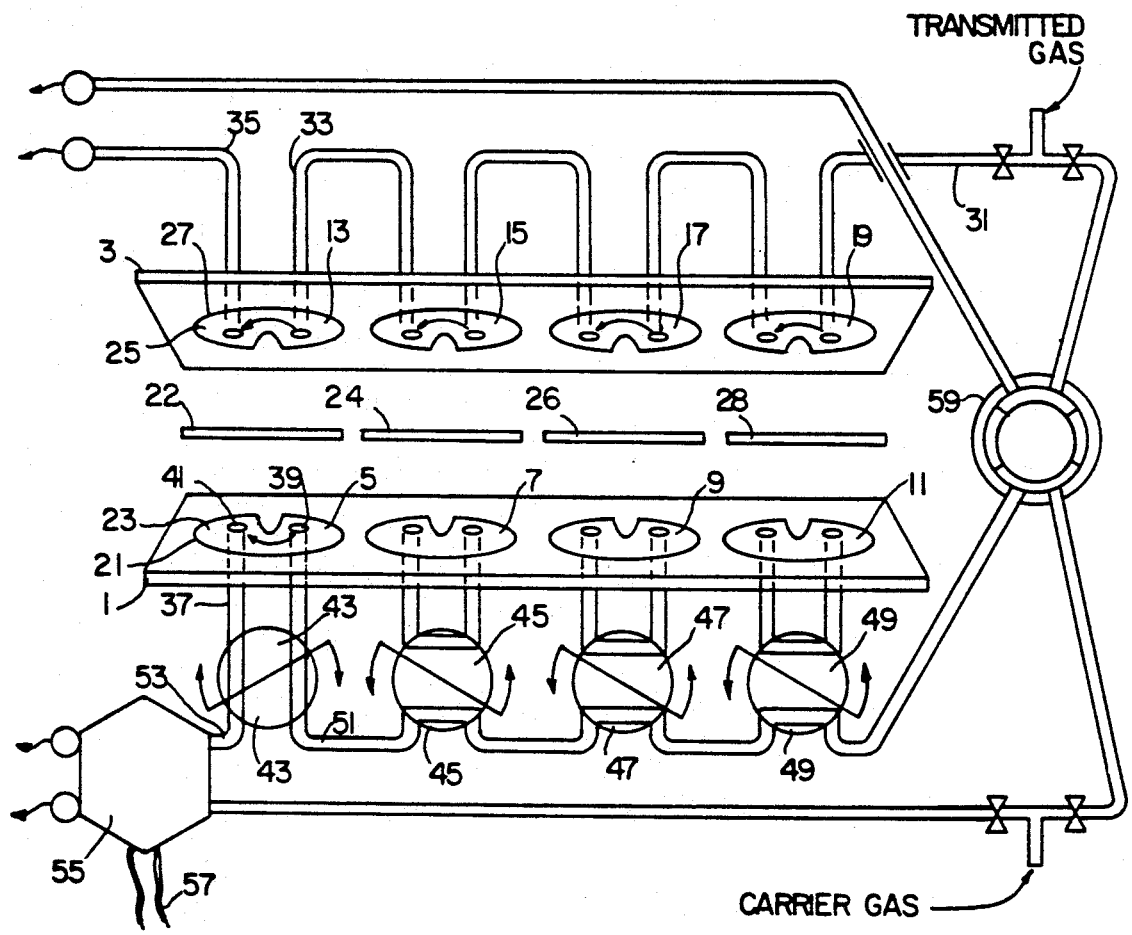
FIG. 1 is a highly simplified schematic diagram of the apparatus in accordance with this invention.
Figure 2:
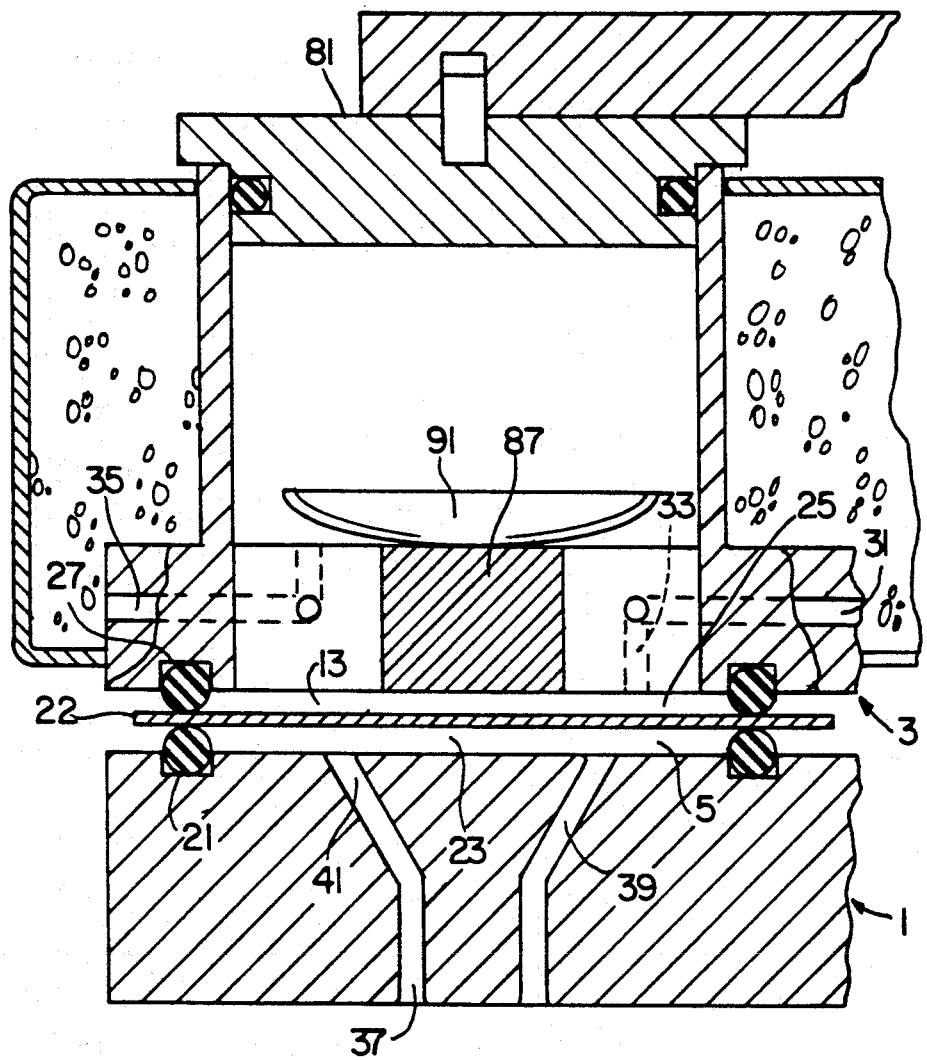
FIG. 2 is a cross-sectional view of a sample site in accordance with this invention.

FIG. 1 of the drawings is a highly simplified schematic drawing of the apparatus in accordance with this invention. The apparatus in accordance with this invention as depicted in FIG. 1 comprises a lower staging section 1 and an upper staging section 3 with a plurality of sample sites on the lower staging section 5, 7, 9 and 11 with complementary sample sites 13, 15, 17 and 19 on upper staging section 3. Sandwiched between lower staging section 1 and upper staging section 3 is a plurality of samples illustrated here as 22, 24, 26 and 28. Each sample site has perimeter defining means which is illustrated at site 5 as 21. Perimeter defining means 21 in site 5 as with the remainder of the sites is preferably an O-ring which is seated into a machined section of each staging section. It is thus seen that when sample 22 is sandwiched between the upper and lower staging sections a first containment volume 23 is defined between the lower staging section 1 and film sample 22. A second gas containment volume 25 is in a similar manner defined by perimeter defining means 27 of the upper staging section at site 13 on the opposite side of film sample 22. These volumes and the communication therethrough are best illustrated in FIG. 2 of the drawings which illustrates sample 22 clamped between staging sections 1 and 3.

The purpose of the FIG. 1 arrangement is to measure the transmission rate of a transmitted gas from the upper staging section gas containment volumes, e.g. second gas containment volume 25 of site 13 through sample 22, into the first gas containment volume 23. For this purpose, a transmitted gas is passed into the gas containment volume of the upper staging section through conduit means 31 machined into upper staging section 3. The transmitted gas for purposes of illustration enters second gas containment volume 25 through entrance 33 and exits through exit 35 and provides a continuous flow across the sample 22 due to the convoluted shape of perimeter defining means 27. As will be further apparent from the following description, the transmitted gas for purposes of this description can be either a gas which is purposely introduced into the sample sites or a volatile solid or liquid which is positioned on means for holding such substances within the sample site.

In a similar manner, lower staging section 1 defines a plurality of conduit means in communication with the first gas containment volumes of each sample site so as to provide communication with a carrier gas. In a manner similar to that described with respect to the upper staging section, the conduit means defined within the lower staging section 1 provides an entrance 39 into a first gas containment volume and an exit 41 therefrom through conduit means 37. The plurality of conduit means within the lower staging section each communicate with a means for interrupting 43, 45, 47 and 49 the flow of carrier gas into and out of each first gas containment volume. Each of the means for interrupting illustrated in FIG. 1 of the drawings is preferably a four way four port valve which provides for either transmission of gas through the first gas containment volume of each sample site or a straight pass through with the flow of gas through the gas containment volume being interrupted.

In the FIG. 1 view, it is seen that site 5 has a path through, while sites 7, 9 and 11 have gas stagnated within the first gas containment volume of such sites. It has been found that the selection of appropriate valves for interrupting the flow of gas into and out of the first gas containment volume is highly critical. Such valves must be capable of maintaining and containing gases of small molecular size. For example, helium is frequently desired as a carrier gas. Few four way port valves are capable of containing helium. A valve operable with helium within the apparatus of this invention has been found to be a four way port valve marketed by the Humphrey Mini-Mizer No. 3E1, modified No. N-519.

At site 5 of lower staging section 1, the means for interrupting in the position indicated communicates through port 51 with a source of carrier gas which passes through first gas containment volume 23 of site 5 and thus exits through port 53 which thus receives gas from the first gas containment volume 23 of the site 5.

Exit port 53 of means for interrupting 43 communicates with means for detecting the presence of a transmitted gas in the carrier gas. In a like manner each exit port of the other means for interrupting illustrated at 45, 47 and 49 establishes similar communication with means for detecting 55. Preferably the means for detecting is a conventional thermal conductivity detector which indicates the presence of a transmitted gas within a carrier gas due to the difference in thermal conductivity of the gas contained therein. Detection means 55 preferably has a voltage output illustrated at 57 for purposes of recording the output on a strip chart recorder.

A preferred detection means is a thermal conductivity detector of the type sold by Gow-Mac under No. 10-952 utilizing gold tungsten filaments for detecting the thermal conductivity of the gases passing therethrough.

Each of the means for interrupting 43, 45, 47 and 49 are automated by means of timers not illustrated in FIG. 1, so as to provide for intermittent opening and closing of each so as to measure the quantity of transmitted gas in each of the second gas containment volumes of the lower staging section. The automation thereof will be described with reference to FIG. 3 of the drawings. The apparatus is automated so as to provide for one gas containment volume at a time to be in communication with detection means 55. Thus as illustrated in FIG. 1 of the drawings, gas containment volume 23 is in communication with detection means 55. However, upon measurement of the amount of transmitted gas swept from that gas containment volume into detection means 55 means for interrupting 43 is permitted to interrupt the communication with gas containment volume 23 and another of the gas containment volumes of the lower staging section is placed in communication with detection means 55.

In order to provide calibration for detection means 55, a sampling valve 59 is present between the transmitted gas and the carrier gas so as to add a known quantity of transmitted gas into the carrier gas. The output voltage of detection means 55 is thus proportional to the quantity of transmitted gas within the carrier gas which may be quantitatively determined from the relationship to the output provided from the measured volume of transmitted gas provided through sampling valve 59.

In actual operation of the apparatus in accordance with this invention, similar samples are placed at each sample site with each of the samples being generally in the form of a film or membrane having a thickness, for example, within the range of a tenth of a mil to approximately 10 mils. Each of the sample sites are of substantially identical volume such that ideally the output from each sample site should be identical to the output from every other sample site. However, due to imperfections in samples it is preferred to utilize a plurality of samples in order to have an accurate measure of the true characteristics of each sample. For example, some samples may possess pin holes which would give an erroneous indication of the true transmission rate through the material.

After calibrating the detecting means a continuous flow of transmitted gas is established through conduit means 31. Each of the first gas containment volumes are then filled with carrier gas and such gas allowed to stagnate by closing the means for interrupting so as to permit transmitted gas to pass through each of the samples and collect in the stagnated carrier gas.

After a suitable holding period, e.g., 15 minutes, the sample sites are placed one at a time into communication with the means for detecting by opening the means for interrupting. After a first sample site has been flushed and the quantity of transmitted gas measured, that sample site is again filled with carrier gas, closed with carrier gas stagnated therein and a second sample site such as 7 placed in communication with the means for detecting and the quantity of transmitted gas contained therein are measured. This process is repeated a number of times depending on the degree of accuracy required until such time as a clear pattern is established so as to indicate the establishment of an equilibrium transmission at each sample site.

Having generally set forth some essential features of the apparatus in accordance with this invention, a more detailed description will now be given with reference to FIG. 3 of the drawings which will illustrate various advantages not heretofore discussed.

Figure 3:
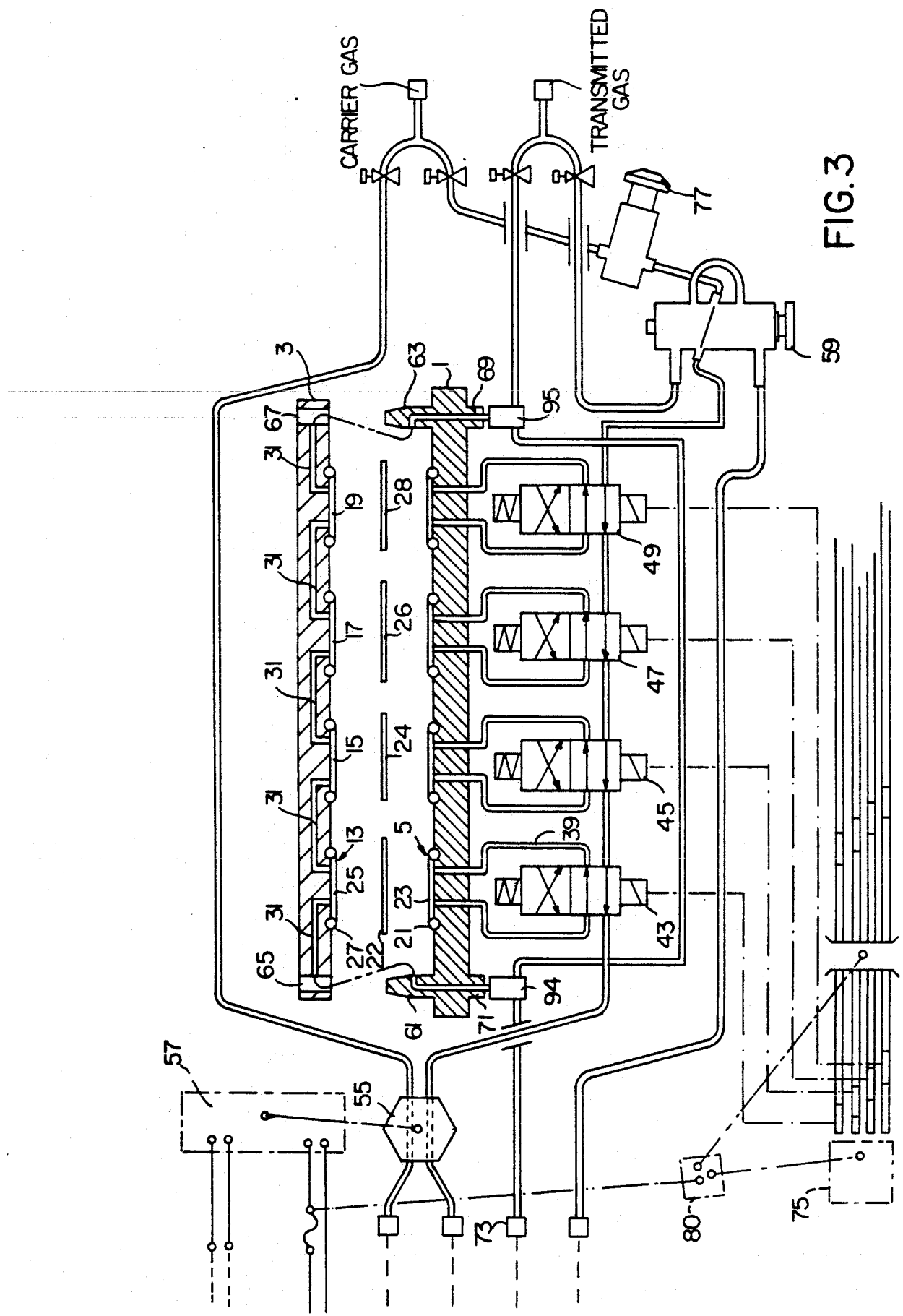
FIG. 3 of the drawings illustrates in greater detail and schematic form the apparatus in accordance with this invention.

A significant advantage of this invention will now become apparent from the FIG. 3 description. The upper staging section 3 in accordance with this invention is removable from the lower staging section without permanent connection thereto of any exterior connection to remainder of the apparatus. The lower staging section 1 is adapted to be located on a semi-permanent basis with all external operational means connected thereto. These unique features are felt to bring about the detection capabilities of this apparatus, as well as greatly simplifying the operation thereof. This aspect of the invention is brought about by alignment pins 61 and 63 of lower staging section 1 which communicate with alignment pin receipt means 65 and 67 of upper staging section 3.

It is thus seen that the transmitted gas communicates with lower staging section 1 through conduit means 69 defined within alignment pin 63 and similar conduit means 71 of alignment pin 61. It is thus seen that the transmitted gas travels through conduit means 69 into conduit means 31 of removable upper staging section 3 when alignment pin 63 is placed within alignment pin receipt means 67 of upper staging section 3. This communication is established by precise machining of both the upper and lower staging sections.

The transmitted gas thus travels into conduit means 31 into sample site 19 and the gas containment volume thereof out through continuation of conduit means 31 into sample site 17 and the gas containment volume thereof continuing through conduit means 31 and into sample site 15 through continuation of conduit means 31 into sample site 13 and the gas containment volume thereof, finally exiting conduit means 31 into the alignment pins defining means 65 and into conduit means 71 of alignment pin 61 of lower staging section 1. The transmitted gas is thus exited from the system at this stage through vent valve 73.

FIG. 3 of the drawings illustrates each of the means for interrupting 43, 45, 47 and 49 in communication with an automated programmable means 75 for opening and closing each of the valves. For example, programming for such device might provide for three minute sweep times through each of the valves with 15 minute soak intervals. An example of a programmable timer 75 operable in embodiments of this invention is marketed by ATC. It is preferred to include within the circuit an interrupter timer 80 such as ATC No. V1540A type No. 322B05A which makes the apparatus operational for either 15 or 30 minute soak periods so as to provide an overall cycle time of 18 or 33 minutes. Such automated means 75 preferably provides for continuous recycling until an operator disconnects the unit. While a particular commercially available timer and interrupter has been specified above, it is readily apparent that any dedicated microprocessor might be utilized so as to vary the soak times from very small periods of time to long periods of time.

A feature illustrated in FIG. 3 of the drawings not previously discussed is an optional injection port 77 which permits hypodermic injection of any desired gases into the system through a conventional septa material.

The description will now be given of the use of the sample sites 13, 15, 17 and 19 of the upper staging section 3 for containing volatile solids and liquids for the purpose of measuring the permeation of such volatile substances through the sample film as illustrated at 22 in FIGS. 4 and 5. For purposes of simplicity, the drawings are in detail for sample sites 13 and 15 only, it being understood that sample sites 17 and 19 are of similar geometry.

Figure 4:
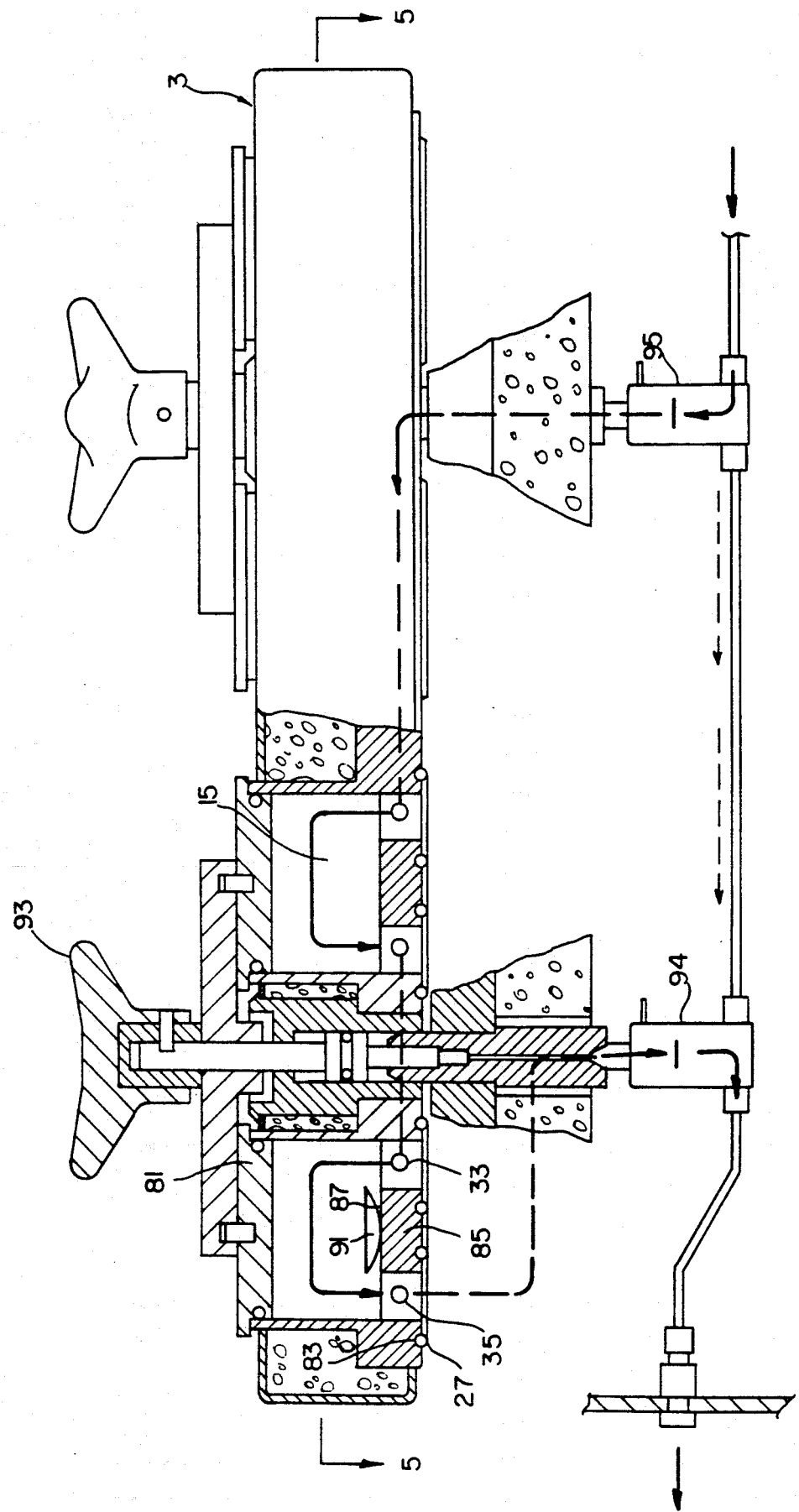
FIG. 4 of the drawings is a cutaway view of a sample site of the upper staging section in accordance with this invention.
Figure 5:
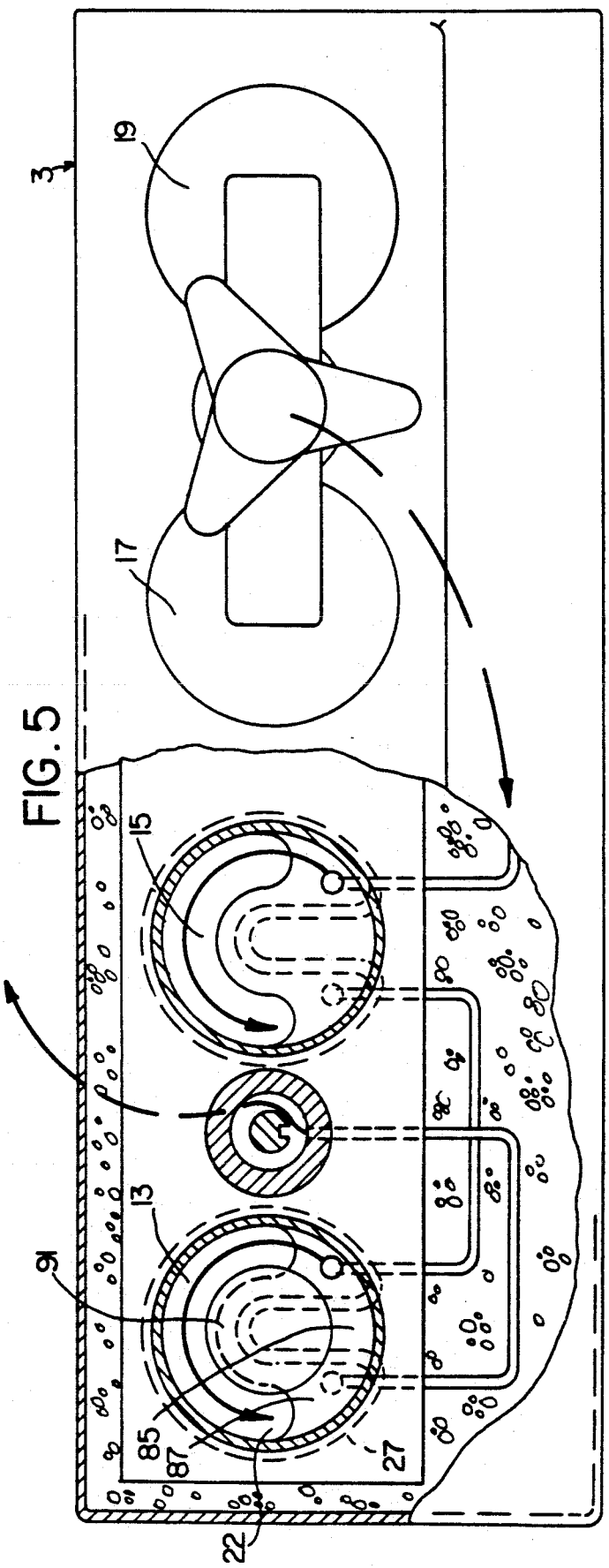
FIG. 5 of the drawings is a view along the line 55 of FIG. 4.

By viewing FIG. 4 of the drawings it is seen that sample site 13 is defined by the boundaries between the sample 22 and removable lid 81. Sample 22 is contacted by perimeter defining means 27, preferably an "O" ring which is in a sinuous configuration as best illustrated in phantom in FIG. 5. It is seen that the perimeter defining means 27 is retained within a recess 83 defined with an upper staging section 3, but diverges inwardly beneath sample holding means 85. The upper surface 87 of sample holding means 85 provides a surface on which a volatile liquid or solid substance may be placed. For example, a dish 91 is illustrated in FIGS. 4 and 5 which may retain a volatile liquid or solid substance.

Site 13 is hermetically sealed by removable lid 81 which is clamped into place by "T" clamp 93 which is also utilized to position upper staging section 3 with respect to the lower staging section 1.

It is preferred when measuring the transmission rate of a volatile substance through the sample 22 to initially place the sample as at 91 on sample holding means 85 and to then seal the sample site 13 by placement of removable lid means 81 thereon. Upon sealing the sample sites, all sample sites are simultaneously flushed with an inert or pursing gas and the system then closed by closing automatic valves 94 and 95. The permeation of the substance through sample 22 then proceeds in the manner previously described.

By providing means for placement of a volatile liquid or solid within the sample site, it is possible to not only measure the permeation of various gases through sample films, but to also measure the permeation of the contained volatile liquid or solid substance through the sample as well.

While the invention has been described and illustrated with four sample sites, it is understood that any number of sample sites may be utilized with this invention. An important aspect of this invention is the provision of forming the upper and lower staging sections from a single piece of machined metal. This adds significantly to the precision of the device in that the amount of exterior plumbing is minimized and the introduction of error into the system therefrom concomitantly minimized.

A preferred material of construction of the upper and lower staging sections is anodized aluminum with conduit means machined therein. Copper or brass may also be utilized. However, when small molecular gases are utilized such as helium and hydrogen, it is necessary that high grade stainless steel or anodized aluminum be utilized for containment purposes.

It is thus seen that the apparatus in accordance with this invention automates the measurement of gas transmission rates through membranous and film materials. It is further seen that the apparatus of this invention provides for measurement of transmission rates of volatile solids and liquids through membranous and film materials. It is additionally seen that the apparatus in accordance with this invention minimizes operator manual participation in the process as well as provide an unexpectedly superior precision and reproduceability in measurements obtained therefrom. As the preceding description was highly exemplary in nature rather than limiting, the spirit and scope of the invention is to be limited only by the following appended claims:

That which is claimed is:

1. An apparatus for measuring gas transmission through membrane samples located at sample sites comprising:

a lower staging section, said lower staging section defining a plurality of sample sites;

each sample site having perimeter defining means for hermetically sealing said sample within said sample site;

said perimeter defining means together with one surface of a sample defining a first gas containment volume;

said lower staging section defining conduit means in communication with each said first gas containment volume for providing a flow of gas into and out of said first gas containment volume;

means communicating with said conduit means for interrupting said flow of gas into and out of each said first gas containment volume so as to provide stagnation of gas within each said first gas containment volume when said means for interrupting is actuated;

each said means for interrupting communicating with a source of gas for introduction into each of said first gas containment volume and having an exit port which receives gas from said gas containment volume when not interrupted;

detection means in communication with said exit port;

said lower staging section defining upwardly projecting alignment pins;

a removable upper staging section defining a plurality of sample sites for alignment with the sample sites of said lower staging section;

said upper staging section having a plurality of perimeter defining means at each sample site for hermetically sealing a sample at said sample site;

said perimeter defining means of said upper staging section together with the other surface of a sample defining a second gas containment volume whereby a sample is contained at each sample site between the perimeter defining means of said lower staging section and the perimeter defining means of said upper staging section;

said upper staging section defining conduit means communicating with said second gas containment volume for providing a flow of gas therethrough;

said upper removable staging section defining alignment pin receipt means for positioning said upper removable staging section upon said lower staging section; and, a removable lid section for each said sample site of said upper staging section for placement of a volatile solid or liquid substance within said sample site.

* * * * *